US010232117B2

(12) United States Patent
Halseth

(10) Patent No.: US 10,232,117 B2
(45) Date of Patent: Mar. 19, 2019

(54) APPARATUSES AND METHOD FOR INJECTING MEDICAMENTS

(71) Applicant: Action Medical Technologies, LLC, Shingle Springs, CA (US)

(72) Inventor: Thor Rollings Halseth, Shingle Springs, CA (US)

(73) Assignee: Action Medical Technologies, LLC, Shingle Springs, CA (US)

( * ) Notice: Subject to any disclaimer, the term of this patent is extended or adjusted under 35 U.S.C. 154(b) by 0 days.

(21) Appl. No.: 15/755,954

(22) PCT Filed: Dec. 18, 2017

(86) PCT No.: PCT/US2017/066957
§ 371 (c)(1),
(2) Date: Feb. 27, 2018

(87) PCT Pub. No.: WO2018/125629
PCT Pub. Date: Jul. 5, 2018

(65) Prior Publication Data
US 2018/0339109 A1 Nov. 29, 2018

Related U.S. Application Data

(60) Provisional application No. 62/478,708, filed on Mar. 30, 2017, provisional application No. 62/439,206, filed on Dec. 27, 2016.

(51) Int. Cl.
*A61M 5/00* (2006.01)
*A61M 5/20* (2006.01)
(Continued)

(52) U.S. Cl.
CPC ...... *A61M 5/3129* (2013.01); *A61M 5/31578* (2013.01); *A61M 5/322* (2013.01);
(Continued)

(58) Field of Classification Search
CPC ............ A61M 5/3129; A61M 5/31578; A61M 5/322; A61M 5/31511; A61M 5/3202; A61M 5/3213; A61M 2005/208
See application file for complete search history.

(56) References Cited

U.S. PATENT DOCUMENTS 3,572,336 A 3/1971 Hershberg
3,742,948 A 7/1973 Post et al.
(Continued)

OTHER PUBLICATIONS

International Search Report and Written Opinion issued in connection with International patent application No. PCT/US2017/066957, dated Feb. 14, 2018, 12 pages.

*Primary Examiner* — Nathan R Price
*Assistant Examiner* — Justin L Zamory
(74) *Attorney, Agent, or Firm* — Duane Morris LLP

(57) ABSTRACT

An injector for delivering a medicament includes an outer sleeve, an inner sleeve, and a syringe. The inner sleeve is disposed partially within the outer sleeve. A plunger rod of the syringe is engaged with the outer sleeve in a fixed spatial relationship such that the plunger rod and the outer sleeve translate as a unit. The outer sleeve is configured for axial translation relative to the inner sleeve from a first configuration wherein the inner sleeve extends from the outer sleeve a first distance to a second configuration in which the inner sleeve extends from the outer sleeve a second distance that is less than the first distance. Further, in a third configuration the inner sleeve extends from the outer sleeve a third distance that is greater than the second distance and the inner sleeve is restricted from axially translating with respect to the outer sleeve.

20 Claims, 20 Drawing Sheets

(51) Int. Cl.
*A61M 5/31* (2006.01)
*A61M 5/315* (2006.01)
*A61M 5/32* (2006.01)
*A61M 5/34* (2006.01)
*A61M 5/50* (2006.01)

(52) U.S. Cl.
CPC ....... *A61M 5/31511* (2013.01); *A61M 5/3202* (2013.01); *A61M 5/3213* (2013.01); *A61M 2005/208* (2013.01)

(56) References Cited

U.S. PATENT DOCUMENTS

| | | | |
|---|---|---|---|
| 4,031,893 A | 6/1977 | Kaplan et al. | |
| 4,447,231 A | 5/1984 | Bekkering | |
| 4,529,403 A | 7/1985 | Kamstra | |
| 4,998,924 A | 3/1991 | Ranford | |
| 5,271,744 A | 12/1993 | Kramer et al. | |
| 5,320,609 A | 6/1994 | Haber et al. | |
| 5,478,316 A | 12/1995 | Bitdinger et al. | |
| 5,637,094 A | 6/1997 | Stewart et al. | |
| 5,957,896 A | 9/1999 | Bendek et al. | |
| 6,159,181 A | 12/2000 | Crossman et al. | |
| 6,319,234 B1 | 11/2001 | Restelli et al. | |
| 6,808,507 B2 | 10/2004 | Roser | |
| 7,381,201 B2 | 6/2008 | Gilbert et al. | |
| 7,517,334 B2 | 4/2009 | Jacobs et al. | |
| 7,717,877 B2 | 5/2010 | Lavi et al. | |
| 7,905,352 B2 | 3/2011 | Wyrick | |
| 7,931,618 B2 | 4/2011 | Wyrick | |
| 8,123,724 B2 | 2/2012 | Gillespie, III | |
| 8,187,224 B2 | 5/2012 | Wyrick | |
| 8,313,463 B2 | 11/2012 | Barrow et al. | |
| 8,343,103 B2 | 1/2013 | Moser | |
| 8,460,245 B2 | 6/2013 | Guillermo et al. | |
| 8,491,530 B2 | 7/2013 | Maritan | |
| 8,529,499 B2 | 9/2013 | Matusch | |
| 8,529,510 B2 | 9/2013 | Giambattista et al. | |
| 8,679,061 B2 | 3/2014 | Julian et al. | |
| 8,845,594 B2 | 9/2014 | Jennings | |
| 9,044,553 B2 | 6/2015 | James et al. | |
| 9,186,459 B2 | 11/2015 | Bechmann et al. | |
| 9,216,256 B2 | 12/2015 | Olson et al. | |
| 9,265,886 B2 | 2/2016 | Wyrick | |
| 9,283,326 B2 | 3/2016 | Kemp et al. | |
| 9,364,617 B2 | 6/2016 | Riedel | |
| 9,421,337 B2 | 8/2016 | Kemp et al. | |
| 9,486,582 B2 | 11/2016 | Abry et al. | |
| 2006/0189938 A1* | 8/2006 | Hommann | A61M 5/2033 604/137 |
| 2010/0016793 A1 | 1/2010 | Jennings et al. | |
| 2010/0298768 A1 | 11/2010 | Halili, Jr. et al. | |
| 2012/0101475 A1 | 4/2012 | Wilmot et al. | |
| 2013/0123710 A1 | 5/2013 | Ekman et al. | |
| 2013/0310759 A1 | 11/2013 | Hourmand et al. | |
| 2014/0135705 A1 | 5/2014 | Hourmand et al. | |
| 2014/0228769 A1 | 8/2014 | Karlsson et al. | |
| 2015/0025474 A1 | 1/2015 | Riedel et al. | |
| 2015/0246181 A1 | 9/2015 | Fourt et al. | |
| 2015/0265782 A1 | 9/2015 | Riedel et al. | |
| 2015/0283323 A1 | 10/2015 | Young et al. | |
| 2016/0008542 A1 | 1/2016 | Hirschel et al. | |
| 2016/0008546 A1 | 1/2016 | Rekaya et al. | |

\* cited by examiner

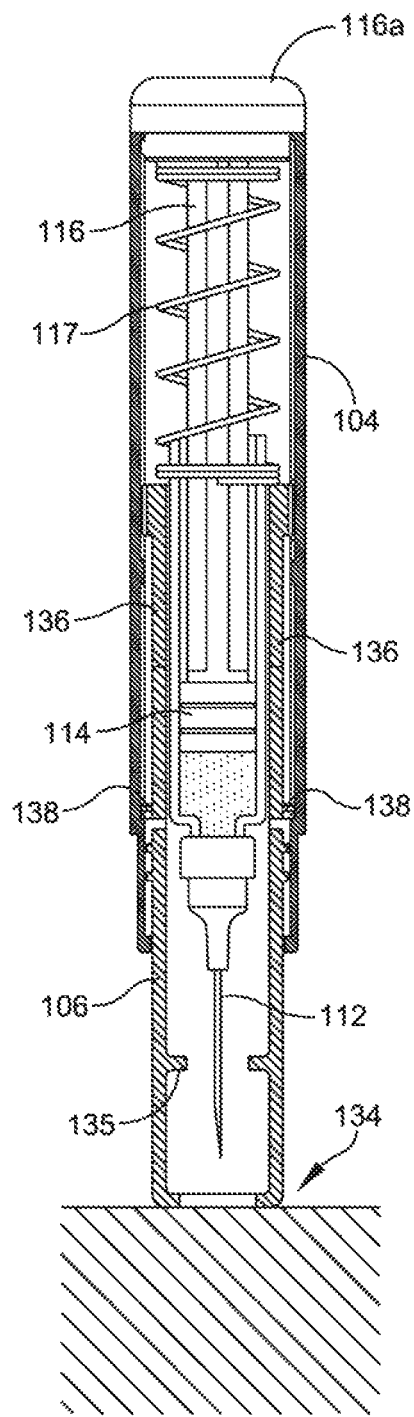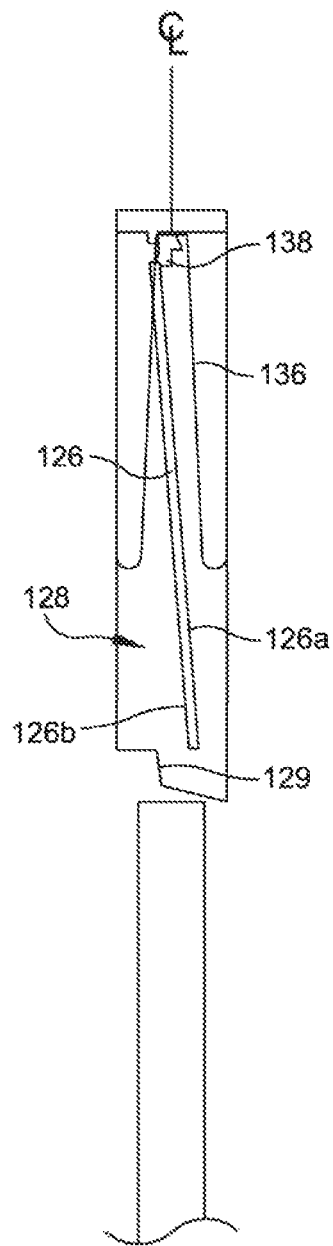
FIG. 5A
FIG. 5B

APPARATUSES AND METHOD FOR INJECTING MEDICAMENTS

CROSS-REFERENCE TO RELATED APPLICATIONS

This application is a national phase entry under 35 U.S.C. § 371 of international patent application no. PCT/US2017/066957, filed Dec. 18, 2017 which claims priority to U.S. Provisional Application No. 62/478,708, filed on Mar. 30, 2017 and U.S. Provisional Application No. 62/439,206, filed on Dec. 27, 2016, the entireties of which are incorporated herein by reference.

FIELD

The invention relates to injectors for medicaments. Specifically, to injectors configured to inject a medicament from a syringe.

BACKGROUND

Many methods are used to inject medicaments into a target site. These include syringes, auto-injectors, and drug pumps. The medicament can be injected at a variety of depths. For example, the medicament can be injected into the epidermis, the dermis, the subcutaneous region, or into the muscles (intramuscular). Some of these devices are specifically intended for at home use by a patient. These devices can be used to deliver a variety of medicaments. For example, the injectors can be used for the delivery of epinephrine to patients who are at risk of anaphylaxis. Such devices include the ANAPEN™ injector sold by Lincoln Medical Ltd. of the United Kingdom and the EPIPEN® injector sold by Mylan Inc. of Pennsylvania.

Many injectors use powerful springs to drive a plunger rod into a pre-filled syringe and inject the medicament into the tissue while pushing the injector into the side of the leg or other body location. Some of these injectors have the advantage of shielding the needle before and/or after use, thereby benefiting patients who have a fear of needles. Present injectors can contain more than twenty-six parts and be complicated to assemble due to the amount and complexity of the parts, which results in high prices to the user. The additional parts also increase the chance of failure of these complex devices.

SUMMARY

In one embodiment, an injector for delivering a medicament includes an outer sleeve, an inner sleeve, and a syringe. The outer sleeve defines a longitudinal axis. The inner sleeve is disposed partially within the outer sleeve. The syringe has a barrel, a needle mounted to the distal end of the barrel, a plunger rod, and a seal slidably mounted in the barrel. The plunger rod is engaged with the outer sleeve in a fixed spatial relationship such that the plunger rod and the outer sleeve translate as a unit throughout operation of the injector. The outer sleeve is disposed and configured for axial translation relative to the inner sleeve from a first configuration wherein the inner sleeve extends from the outer sleeve a first distance to a second configuration in which the inner sleeve extends from the outer sleeve a second distance that is less than the first distance. Additionally, in a third configuration the inner sleeve extends from the outer sleeve a third distance that is greater than the second distance and the inner sleeve is restricted from axially translating with respect to the outer sleeve.

In another embodiment, an injector for delivering a medicament includes an outer sleeve, an inner sleeve, and a syringe. The inner sleeve is disposed partially within the outer sleeve. The inner sleeve defines a chamber between a distal end and a proximal end of the inner sleeve and has an engagement member extending into the chamber at a position between the distal end and the proximal end. The syringe has a barrel, a needle mounted to the distal end of the barrel, a plunger rod, and a seal slidably mounted in the barrel. The plunger rod is engaged with the outer sleeve in a fixed spatial relationship such that the plunger rod and the outer sleeve translate as a unit throughout operation of the injector. The outer sleeve is disposed and configured for axial translation relative to the inner sleeve, and in a first configuration the engagement member is spaced apart from the barrel of the syringe. In a second configuration the syringe contacts the engagement member such that continued axial translation of the outer sleeve causes translation of the plunger rod relative to the barrel to cause delivery of the medicament through the needle.

In another embodiment, a method for operating an injector to deliver a medicament to a target location includes the step of placing a distal end of an inner sleeve against the target location. The method also includes the step of applying a force to an outer sleeve. Applying the force to the outer sleeve causes axial translation of the outer sleeve and a syringe relative to the inner sleeve. Applying the force also causes a needle of the syringe to extend out from the distal end of the inner sleeve and into the target location. The force also causes the syringe to contact an engagement member of the inner sleeve. The method also includes the stop of applying a continued force to the outer sleeve. Applying the continued force to the outer sleeve causes translation of a plunger rod and a seal within the syringe to cause delivery of the medicament. The method also includes the step of removing the injector from the target location. Upon removal, a biasing member applies a force on the inner sleeve to cause the inner sleeve to translate in the distal direction with respect to the outer sleeve to cover the needle of the syringe such that the inner sleeve is locked in place with respect to the outer sleeve.

BRIEF DESCRIPTION OF THE DRAWINGS

These and other features of the devices and methods provided herein will be more fully disclosed in, or rendered obvious by, the following detailed description of the preferred embodiment of the invention, which is to be considered together with the accompanying drawings wherein like numbers refer to like parts and further wherein:

FIG. 5A is a cross-sectional view of the injector of FIG. 1 in an initial configuration;

FIG. 5B is a detail view of the flex arm and raised curb in the initial configuration;

DETAILED DESCRIPTION

Figure 1:
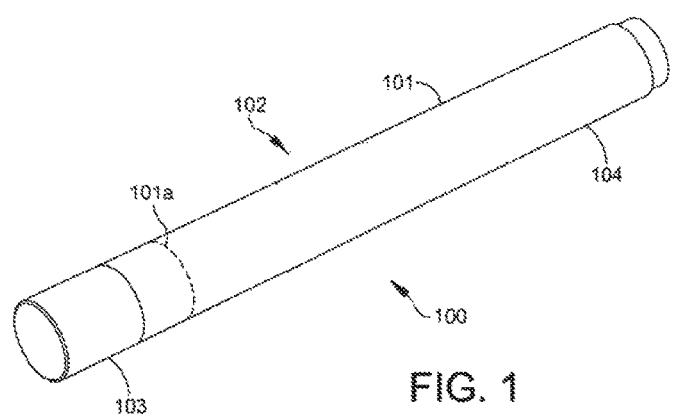
FIG. 1 is an isometric view of one embodiment of an injector for a medicament.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures. The terms "medicament" or "drug" as used herein refers to any substance for delivery to a target. For example, these terms include anticoagulants, vaccines, biologics, and any injectable fluid.

The present disclosure provides an injector for injecting medicament into a target site. The injector provides for easy use by a patient or other caregiver and is configured for reliable use after being stored for long periods of time. In addition, because the injector utilizes a low number of parts, it is inexpensive and easy to manufacture. The injectors described herein can be used to deliver, for example, epinephrine, ketamine, moxifloxacin, ertapenem, atropine, diazepam, or naloxone.

FIG. 1 shows an isometric view of an injector 100 in an as-shipped configuration. The injector 100 includes a body 102, and a cap 103. With the cap 103 engaged with the body 102, it is not possible to operate the injector 100 to distribute the contents of the injector 100. The injector can also include a label 101. The label 101 can wrap around both the body 102 and at least a portion of the cap 103 to prevent inadvertent removal of the cap 103. In addition, this arrangement of the body 102, cap 103, and label 101 can maintain the sterility of the syringe contained within the injector 100. The label can include a perforated portion 101a which allows for the tearing of the label 101 and removal of the cap 103. The perforation can be positioned at approximately the proximal end of the cap 103, thereby allowing for the tearing of the label 101 and removal of the cap 103. The label 101 can be torn at the perforations by, for example, rotation of the cap 103 with respect to the body 102, as shown in FIG. 1B. In some embodiments, the perforations do not pass fully through the label 101 (i.e., the perforations only partially pass through the label). In such embodiment, by enveloping the body 102 and the cap 103 with the label 101, the inflow of materials to the injector 100 is restricted. For example, the label 101 may provide water resistance which prevents water from entering the injector. This advantageously protects the contents of the injector 100.

Figure 2:
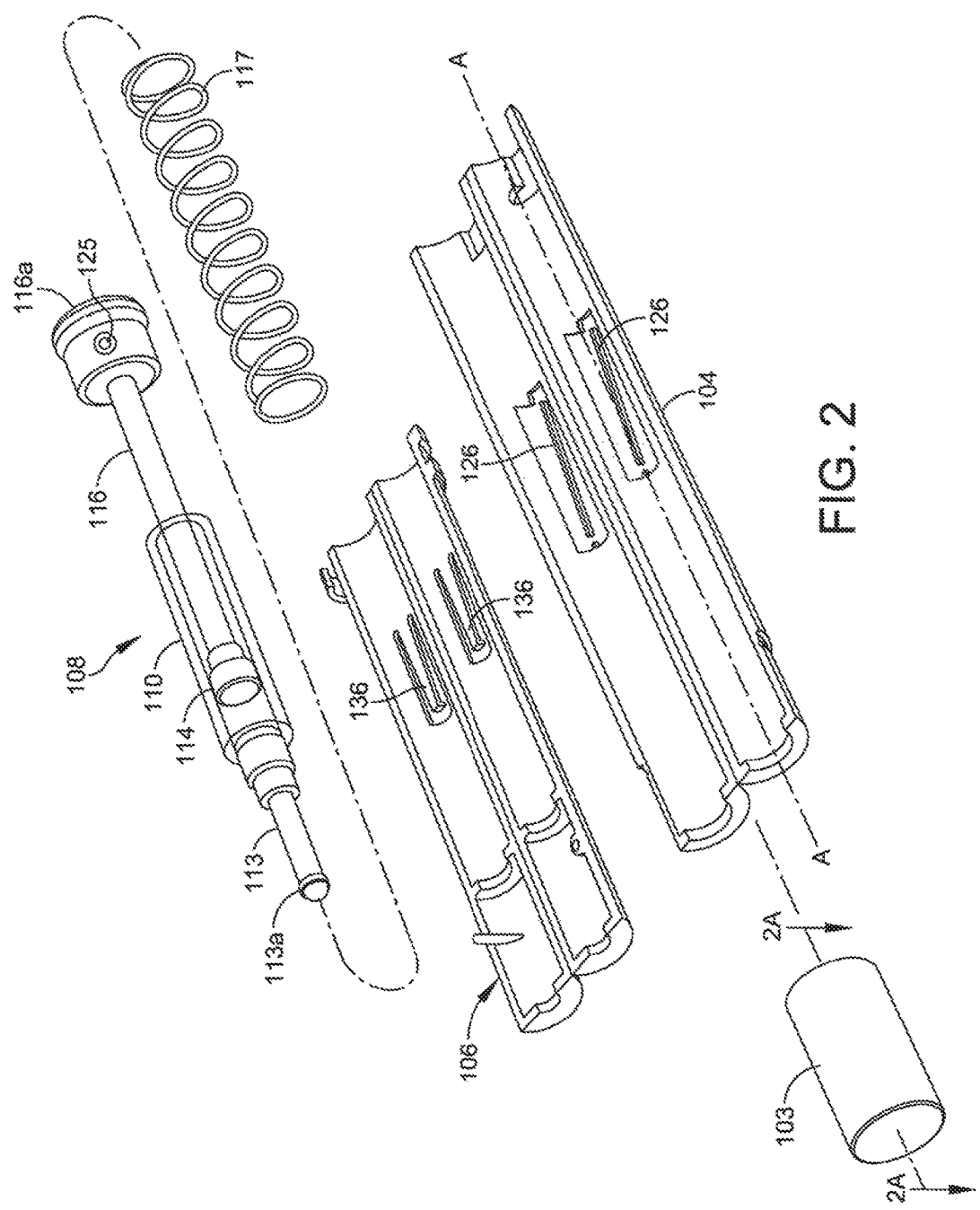
FIG. 2 is an exploded view of the injector of FIG. 1.

As can be seen in the exploded view of FIG. 2, the body 102 includes an outer sleeve 104 and an inner sleeve 106. A syringe 108 is disposed within the body 102. The outer sleeve 104 defines a longitudinal axis A. After assembly, the inner sleeve 106 is disposed partially within the outer sleeve 104. The outer sleeve 104 and the inner sleeve 106 are, in the illustrated embodiment, generally cylindrical in shape. However, the outer sleeve 104 and inner sleeve 106 can be of any appropriate shape, with the shape being chosen to provide the desired external appearance.

The syringe 108 is pre-filled with a medicament and includes a barrel 110, a needle 112 (shown in FIG. 5A), a needle cover 113, a seal 114, and a plunger rod 116. The syringe 108 is pre-filled with a medicament. The barrel 110 can be a glass barrel, such as those constructed from straight cane glass. Alternatively, the barrel 110 can be constructed of a polymeric material. The barrel 110 can be coated with a material to reduce chemical interactions between the barrel 110 and the medicament. The needle 112 is mounted at the distal end of the barrel 110 and defines a lumen through which medicament can be delivered from the barrel 110 to the target site. The needle 112 can be attached to the barrel 110 using any appropriate method, such as staking and adhesives. The seal 114 is disposed within the barrel 110 and is configured for axial translation within the barrel 110. The seal 114 can be constructed of an elastomeric material and provide a seal against the inner wall of the barrel 110 to maintain the sterility of the medicament prior to use. The plunger rod 116 is engaged with the seal and includes an elongated portion which extends from the proximal end of the barrel 110 and a cap 116*a*.

Figure 1A:
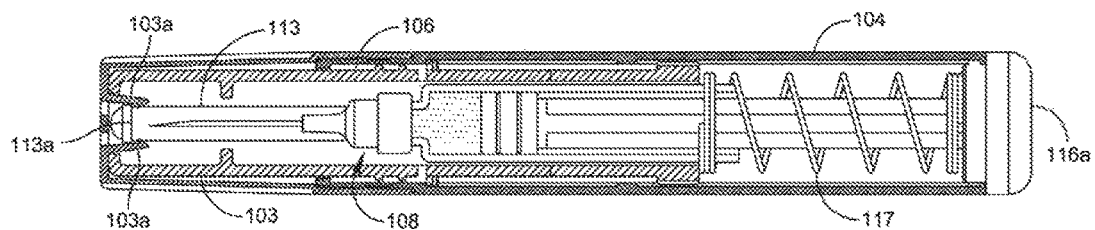
FIG. 1A is a cross-sectional view of the injector of FIG. 1.
Figure 1B:
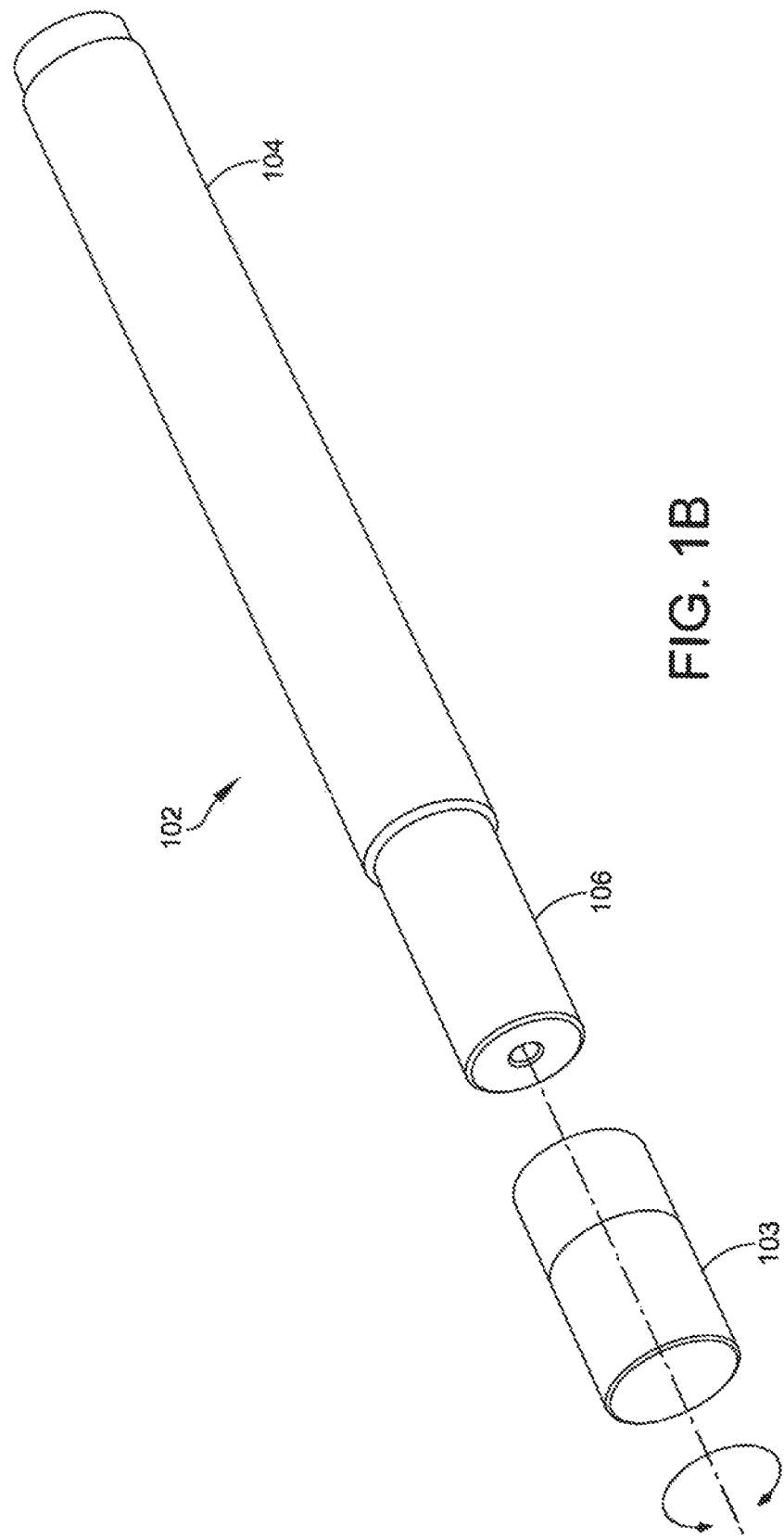
FIG. 1B is an isometric view of the embodiment of FIG. 1 with the cap removed.
Figure 2A:
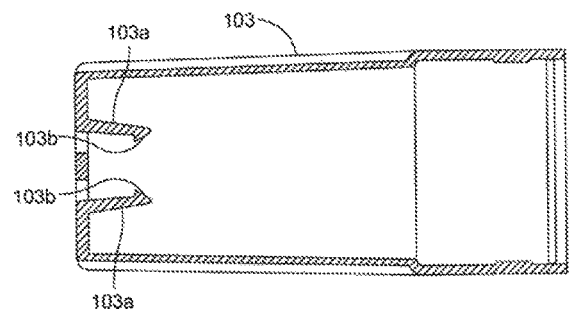
FIG. 2A is a cross-sectional view of a cap.

In the as-shipped configuration, as shown in FIG. 1A, the cap 103 engages the needle cover 113. Hence, removal of the cap 103 from the body removes the needle cover 113 from the syringe. As shown in FIG. 2A, the cap 103 includes projections 103*a* which engage the distal end of the needle cover 113. The needle cover 113 can include a flange 113*a* adjacent its distal end. The projections 103*a* can include teeth 103*b* which are configured to engage the flange 113*a*. As such, when the cap 103 is removed, the needle cover 113 is removed as well. The projections 103*a* pass through an aperture at the distal end of the inner sleeve 106 to provide access to the needle cover 113.

Rotation of the cap 103 with respect to the body 102 during removal can also cause rotation of the needle cover 113 with respect to the syringe 108. This rotation can assist in overcoming any sticking of the needle cover 113 to the syringe 108, thereby making removal of the cap 103 and needle cover 113 easier for the user.

The injector 100 can also include a biasing member 117. The biasing member can be disposed at least partially proximally to the inner sleeve 106 and bias the inner sleeve 106 to an extended position, as shown in FIG. 5A. The distal end of the biasing member 117 can be in contact with the inner sleeve 106, while the proximal end of the biasing member 117 can be in contact with the plunger rod 116 or the outer sleeve 104. The biasing member 117 can be any appropriate member capable of storing and releasing energy. For example, the biasing member 117 can be a spring—such as a coil spring or a helical spring, an elastomeric sleeve, or a flexible arm extending from the outer sleeve 104. As will be described further herein, the biasing member 117 maintains the inner sleeve 106 in the extended position prior to insertion of the needle into the target and also causes the inner sleeve 106 to extend after removal of the injector 100 from the target location. The stiffness of the biasing member 117 can be significantly lower than that used in other injectors. For example, in one embodiment, the biasing member 117 is a compression spring with a spring rate between approximately 0.50 lbs./in. and 0.60 lbs./in. In another embodiment, the spring rate is between approximately 0.25 lbs./in. and 0.75 lbs./in. In another embodiment, the spring rate is between approximately 0.10 lbs./in. and 0.50 lbs./in. The use of a biasing member with lower stiffness than other injectors, the cost of the biasing member itself is reduced. In addition, the cost of other parts of the injector can be lower because they do not need to be configured to withstand the higher forces.

Figure 3:
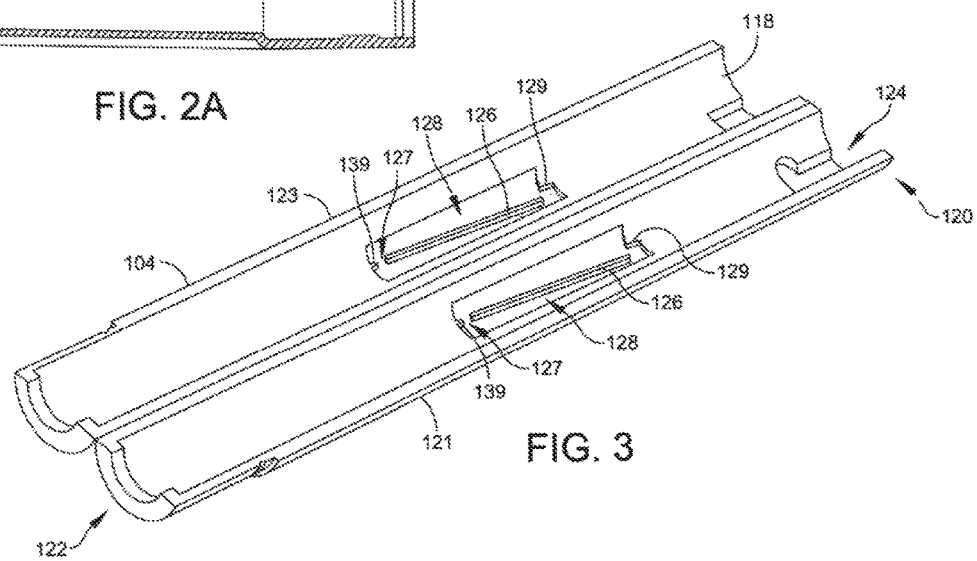
FIG. 3 is an isometric view of an outer sleeve.

As shown in FIG. 3, the outer sleeve 104 has a generally cylindrically shaped sidewall 118 defining a proximal end 120 and a distal end 122. As shown, the outer sleeve can be constructed in a clamshell type arrangement with a first portion 121 connected to a second portion 123 by a living hinge. During assembly, the first portion 121 and second portion 123 are brought together to fixedly close the outer sleeve 104. Alternatively, the first portion 121 and second portion 123 can be separate components (i.e., not connected by a living hinge). In such an embodiment, the separate first portion 121 and second portion 123 are brought together during assembly. The outer sleeve 104 can include features to retain the first portion 121 and second portion 123 in a fixed relationship for storage and use. For example, one of the first portion 121 or the second portion 123 can have flex arms configured to engage recesses or cavities on the opposite portion. Alternatively, the first portion 121 and second portion 123 can be connected using a heat staking process, wherein a stud on one of the first portion 121 and second portion 123 is expanded using heat to fill a hole of the opposite portion. Alternatively, the first portion 121 and the second portion 123 can be welded to one another using ultrasonic welding or another process.

Also during assembly, the plunger rod 116 is engaged with the outer sleeve 104, for example at the proximal end 120. As such, the plunger rod 116 and the outer sleeve 104 are in a fixed spatial relationship such that the plunger rod 116 and the outer sleeve 104 translate as a unit throughout operation of the injector 100. In one embodiment, the sidewall 118 defines a keyway 124 and the plunger rod 116 includes a corresponding key 125. During assembly, the key 125 is disposed in the keyway 124 to prevent relative movement between the plunger rod 116 and outer sleeve 104. Alternatively, the plunger rod 116 can be engaged with the outer sleeve 104 using any appropriate method, including a press fit interface, bonding of the plunger rod to the outer sleeve, a screw thread engagement, or a pin connecting the plunger rod to the outer sleeve.

The outer sleeve 104 also includes a raised curb 126, as shown best in FIG. 3. The raised curb 126 extends from the sidewall 118. The raised curb 126 extends along a path which has a longitudinal component, parallel to longitudinal axis A, and a circumferential component extending along the circumference of the outer sleeve 104. In some embodiments, the raised curb 126 is disposed within a recess 128 in the sidewall 118. The recess 128 allows the raised curb 126 to interface with the inner sleeve 106 without imparting an inward radial force on the inner sleeve 106. Additionally, the recess 128 defines a strike face 129 at the proximal end of the raised curb 126. In at least one embodiment, the outer sleeve 104 includes at least two raised curbs 126. In the illustrated embodiment, the outer sleeve includes two raised curbs 126 which are positioned 180° from each other (directly opposite one another). This creates balanced forces on the inner and outer sleeves.

Figure 4:
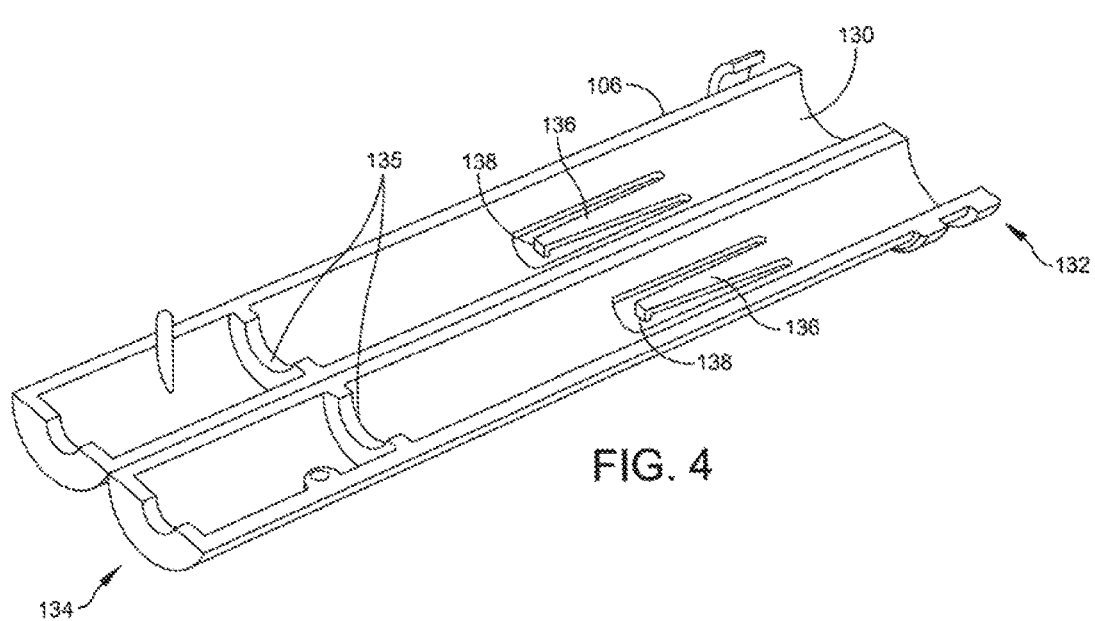
FIG. 4 is an isometric view of an inner sleeve.

The inner sleeve 106 can also be provided in a clamshell configuration as described above with reference to the outer sleeve 104. As shown in FIG. 4, the inner sleeve 106 includes a sidewall 130 defining a proximal end 132 and a distal end 134. As described above, the biasing member 117 can be in contact with the proximal end 132 to bias the inner sleeve 106 to an extended position. The inner sleeve 106 also includes one or more engagement members 135 that extend into a chamber defined within the sidewall 130 between the proximal end 132 and the distal end 134. As will be described in more detail below, the engagement members 135 are configured to contact the syringe 108 during operation to limit the depth of insertion of the needle 112 into the target location. In the embodiment shown, the engagement members 135 are spaced apart from the distal end 134. The distance that the engagement members 135 are spaced apart from the distal end 134 defines the depth of insertion of the needle 112. Hence, the depth of insertion can be accurately controlled during the manufacturing of the inner sleeve 106. Appropriate tolerances can be applied to the distance between the engagement members 135 and the distal end 134 of the inner sleeve 106 to ensure that the injection reaches the desired position in the tissue. For example, in one embodiment, the needle 112 extends approximately 16 mm (0.62 inches) from the distal end of the inner sleeve 106. In another embodiment, the needle 112 extends approximately 25 mm (1.0 inch) from the distal end of the inner sleeve 106. In another embodiment, the needle 112 extends approximately 38 mm (1.5 inches) from the distal end of the inner sleeve 106. The engagement members 135 can be integrally formed with the inner sleeve 106 or, alternatively, can be separate components that are assembled to the inner sleeve 106.

As shown in FIG. 4, the inner sleeve 106 also includes a flex arm 136. The flex arm 136 generally extends parallel to the longitudinal axis A and includes a protrusion 138 extending radially outward, toward the outer sleeve 104. The protrusion 138 interfaces with the raised curb 126 during the operation of the injector 100, as will be described further below. In the illustrated embodiment, the inner sleeve 106 includes two flex arms 136 which are positioned 180° from each other (directly opposite one another). As described above, this ensures that the forces applied to the inner sleeve 106 are balanced.

FIGS. 5A-8C show views of the steps of operation of the injector 100. Prior to use, the cap 103 is removed from the injector 100. Because the cap 103 is engaged with the needle cover 113, removal of the cap 103 removes the needle cover 113 from the syringe 108. The cap and needle cover can now be discarded. Subsequently, as shown in FIG. 5A, the distal end 134 of the inner sleeve 106 is placed against the target location. As seen in FIG. 5A, in this configuration, the inner sleeve 106 extends from the outer sleeve 104 a first distance and covers the needle 112. Additionally, in this configuration, the biasing member 117 is in a relatively de-energized state. In this de-energized state, the biasing member 117 is not applying significant forces to the components of the injector 100. This allows the injector 100 to be stored for extended periods of time without risk of damage to the components therein.

As shown in FIG. 5B, in this initial configuration, the protrusion 138 of the flex arm 136 is initially positioned at the distal end of the raised curb 126. The protrusion is positioned on the first side of the raised curb 126. In this configuration, the flex arm 136 is in an unstressed state (i.e., the interaction of the protrusion 138 with the raised curb 126 does not cause deflection of the flex arm in this configuration). This ensures that these parts do not creep, or take on a permanent deformation, during storage. This allows the device to be stored for extended periods without risk of damaging the components, thereby increasing the reliability of the injector.

Figure 6A:
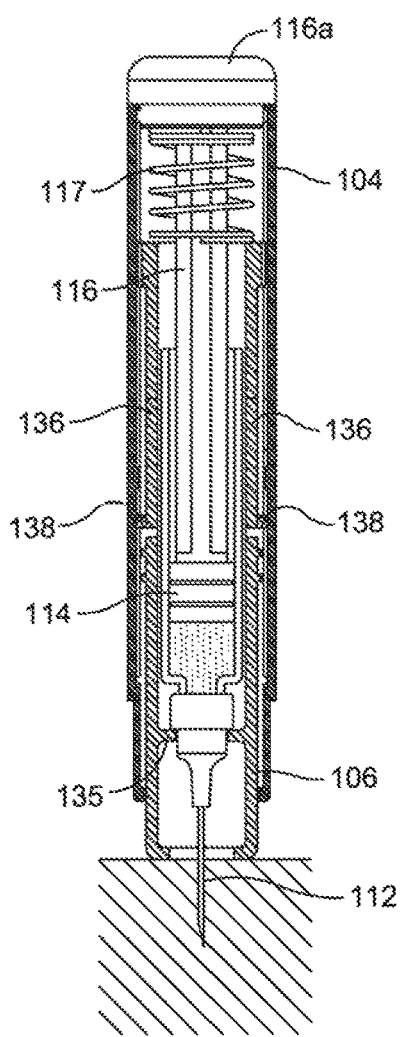
FIG. 6A is a cross-sectional view of the injector of FIG. 1 in a second configuration.
Figure 6B:
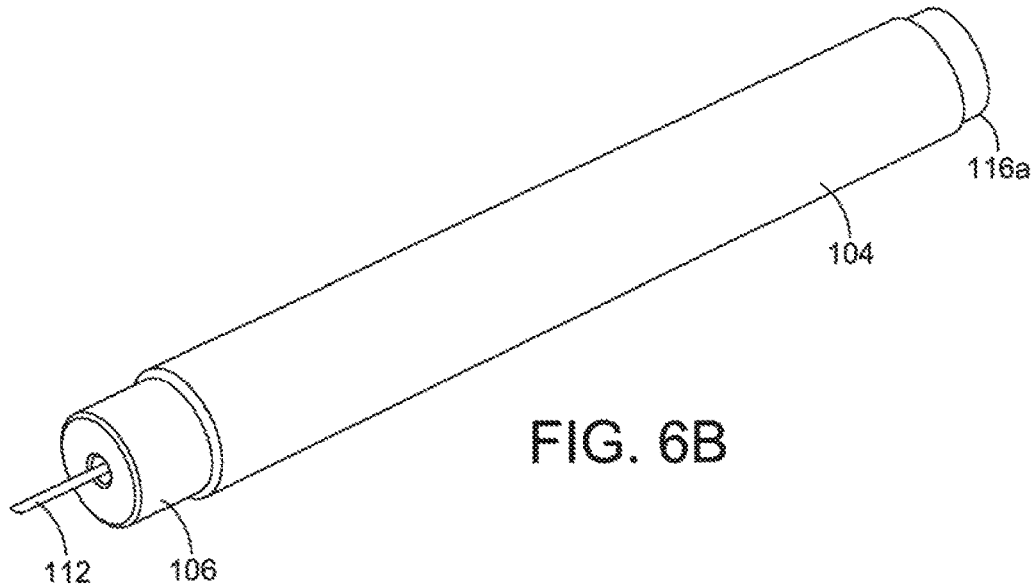
FIG. 6B is an isometric view of the injector of FIG. 1 in the second configuration.

As shown in FIG. 6A, force applied to the outer sleeve in the distal direction causes the outer sleeve 104 to move toward the target location and, hence, causes the extension of the inner sleeve from the outer sleeve to be reduced to a second distance. This can also be seen in the isometric view of FIG. 6B. Because the plunger rod 116 is engaged with the outer sleeve 104, the plunger rod 116 translates with the outer sleeve 104. The plunger rod 116 causes movement of the seal 114 and, because the seal 114 is in sealing engagement with the barrel 110, static frictional forces between the seal 114 and the barrel 110 cause movement of the syringe 108. The syringe 108 translates, with the outer sleeve 104, in the distal direction until the syringe 108 comes in contact with the engagement members 135. This translation of the syringe 108 causes the needle 112 to be inserted into the target location. The engagement members 135 can contact the barrel 110 of the syringe or a crimp cap or other component engaged with the barrel 110. At this point, shown in FIGS. 6A and 6B, continued translation of the syringe barrel 110 is restricted.

Translation from the configuration shown in FIG. 5A to that shown in FIG. 6A causes the biasing member to be compressed or energized, thereby storing energy for later release.

Figure 6C:
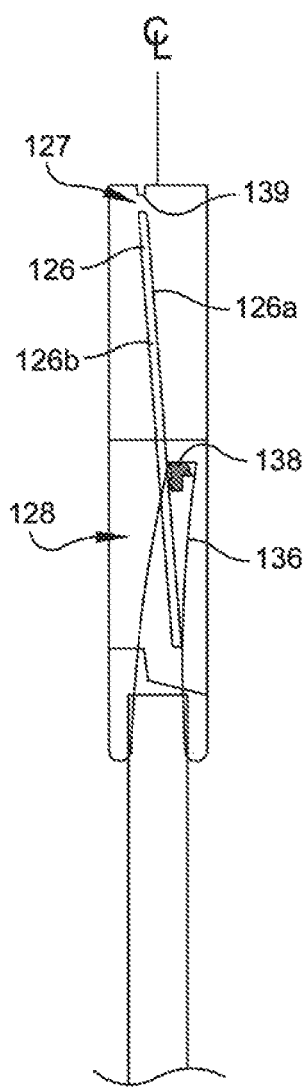
FIG. 6C is a detail view of the flex arm and raised curb in the second configuration.

As shown in FIG. 6C, as the outer sleeve 104 translates with respect to the inner sleeve 106 from the first configuration to the second configuration, the protrusion 138 of the flex arm 136 travels along the first side 126a of the raised curb 126. As it does so, the flex arm 136 is deflected from its unstressed, natural position to the deflected position shown in FIG. 6C.

Figure 7A:
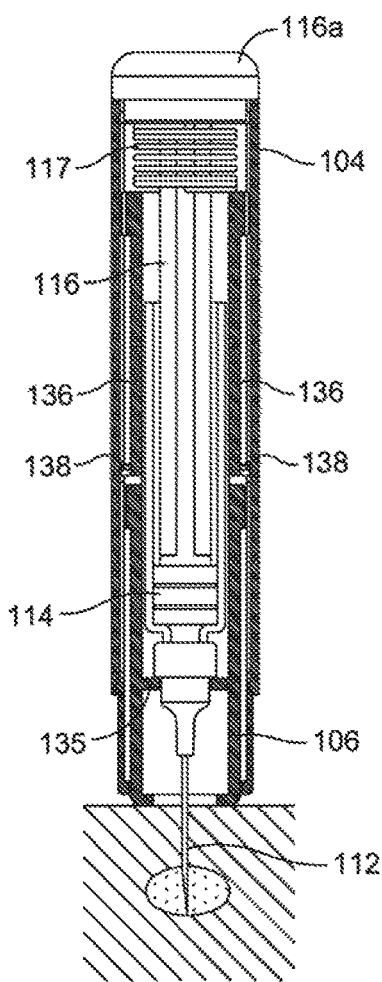
FIG. 7A is a cross-sectional view of the injector of FIG. 1 in a third configuration.
Figure 7B:
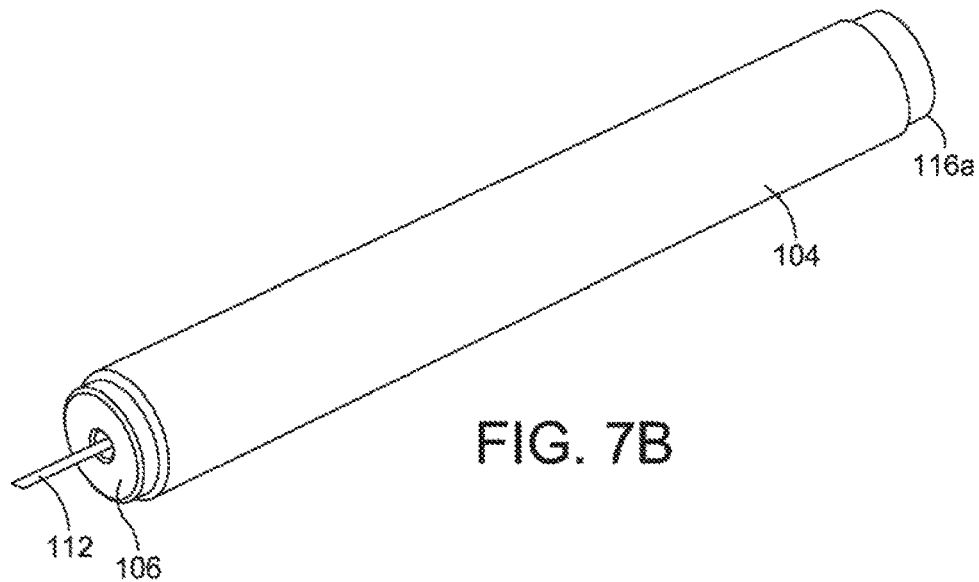
FIG. 7B is an isometric view of the injector of FIG. 1 in the third configuration.

Continued displacement of the outer sleeve 104 causes injection of the medicament, as shown in FIG. 7A. As shown in FIGS. 7A and 7B, the extension of the inner sleeve 106 from the outer sleeve 104 is further reduced. Because the syringe barrel 110 is restricted from further movement by contact with the engagement members 135, continued displacement of the outer sleeve 104 and plunger rod 116, causes the seal 114 to translate within the barrel 110 of the syringe 108. This causes the medicament to be expelled from the barrel 110, through the needle 112, and into the target. Additionally, the biasing member 117 is further compressed or energized.

Figure 7C:
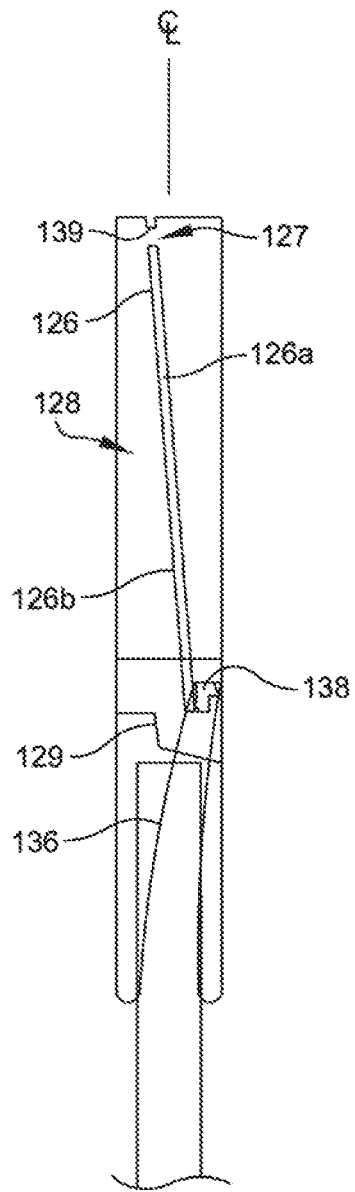
FIG. 7C is a detail view of the flex arm and raised curb just prior to completion of the delivery of the medicament.
Figure 7D:
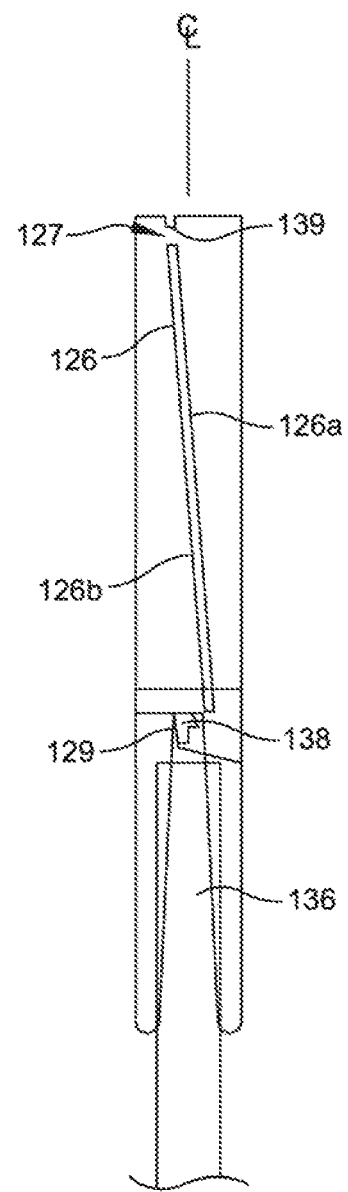
FIG. 7D is a detail view of the flex arm and raised curb just after completion of the delivery of medicament.

As shown in FIG. 7C, this continued translation of the outer sleeve 104 causes the protrusion 138 to reach the proximal end of the raised curb. As shown in the transition from FIG. 7C to FIG. 7D, at completion of expulsion of the medicament, the protrusion 138 disengages from the first side 126a of the raised curb 126. As the protrusion disengages, the elastic energy stored in the flex arm 136 causes the flex arm 136 to return toward its natural position. As it does so, the protrusion 138 or another portion of the flex arm 136 contacts the strike face 129 on the outer sleeve 104. The contact with the strike face 129 provides audible and/or tactile feedback to the user that delivery of the medicament is complete.

Figure 8A:
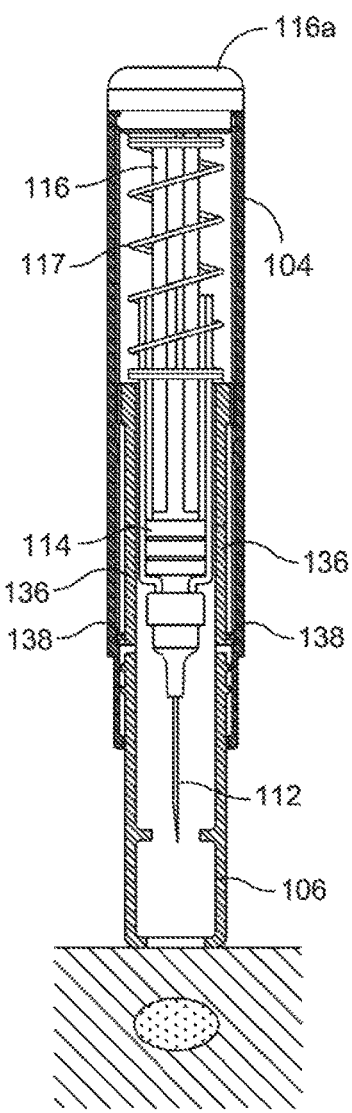
FIG. 8A is a cross-sectional view of the injector of FIG. 1 in a fourth configuration.
Figure 8B:
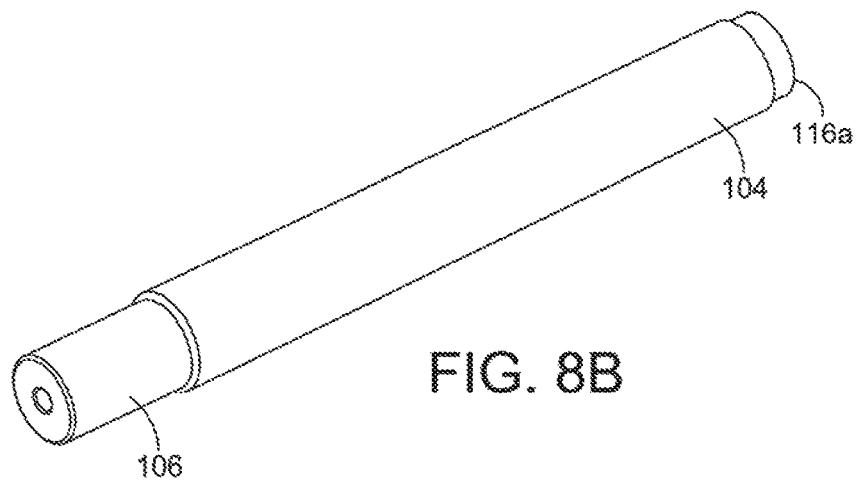
FIG. 8B is an isometric view of the injector of FIG. 1 in the fourth configuration.
Figure 8C:
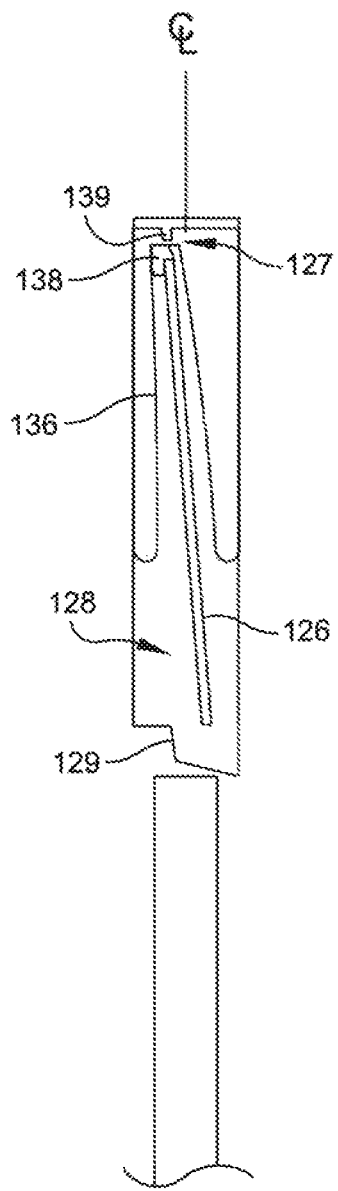
FIG. 8C is a detail view of the flex arm and raised curb in the fourth configuration
Figure 9:
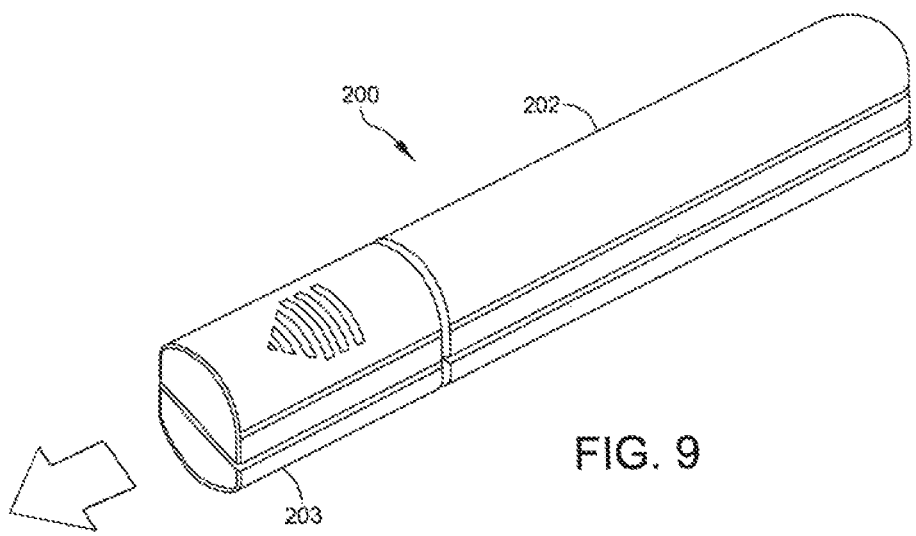
FIG. 9 is an isometric view of another embodiment of an injector.

As shown in FIGS. 8A-8C, after completion of the injection, and removal of the injector 100 from the target, the biasing member 117 de-energizes and causes the inner sleeve 106 to translate in the distal direction with respect to the outer sleeve 104, such that the inner sleeve 106 extends a third distance from the outer sleeve 104. The third distance can be the same as the first distance or, alternatively, can be different. As the inner sleeve 106 extends, it covers the needle 112. Hence, the needle 112 is covered both before and after use of the injector 100. This protects against needle-stick injuries and hides the needle from sight, which is particularly important for patients with a fear of needles.

While the inner sleeve 106 extends, the protrusion 138 travels along the second side 126b of the raised curb 126. Upon full extension of the inner sleeve 106, the protrusion 138 snaps into the cavity 127 formed between the proximal end of the raised curb 126 and a locking member 139. In this position, the protrusion prevents translation of the inner sleeve 106 in either the proximal or distal directions. Hence, the inner sleeve is locked in position and cannot be translated to expose the needle 112. In at least one embodiment, the flex arm 136 is in a stressed or deformed position when the protrusion is disposed in the cavity 127. As a result, the internal forces in the flex arm 136 push the protrusion 138 into the end of the raised curb 126 to further prevent retraction of the inner sleeve 106.

In one embodiment, the protrusion 138 has an "L" shaped cross-section. As a result, a notch is formed that engages the end of the raised curb 126 to lock the flex arm 136 in position.

In other embodiments, as shown in FIGS. 9-13, a syringe with a retractable needle is used. Repetitive description is not included herein, however, such an embodiment can include many of the same features, aspects, and configurations as those described above with respect to the embodiment of FIGS. 1-8C. In such an embodiment, the needle of the syringe is configured to retract into the barrel of the syringe after completion of the injection. One example of such a syringe is the BD INTEGRA® syringe sold by Becton Dickinson of New Jersey. However, any retractable needle syringe can be used. The syringe can either be pre-filled or, alternatively, filled at time of use by drawing medicament from a vial. In the case of a fill at time of use, a vial adapter can be used.

Figure 10:
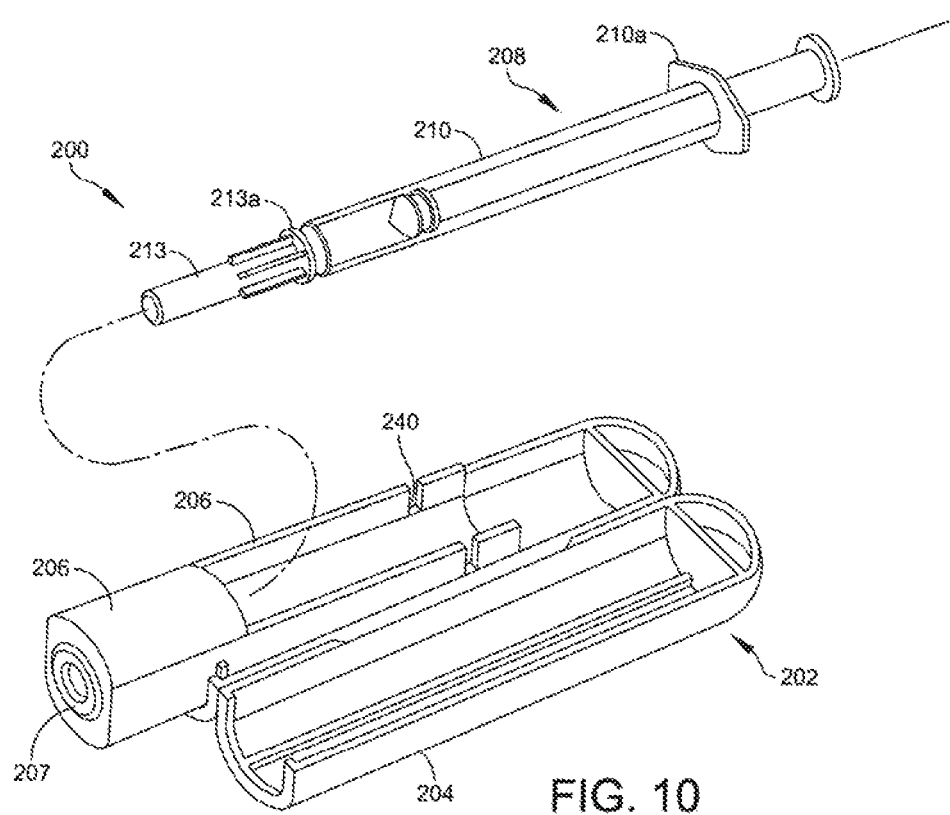
FIG. 10 is an exploded view of the injector of FIG. 9.

The injector 200 of FIGS. 9-12 includes a body 202 and a cap 203. The body 202 includes an outer sleeve 204 and an inner sleeve 206 as well as a needle sleeve 207. The needle sleeve 207 is configured for axial translation within, and with respect to, the inner sleeve 206. The inner sleeve 206 is configured for axial translation within, and with respect to, the outer sleeve 204. As shown in FIG. 10, the syringe 208 is inserted into the body 202 such that the needle 212 of the syringe extends from the distal end of the inner sleeve 206. After the syringe 208 is placed within the body 202, the outer sleeve 204 can be closed.

In this embodiment, the barrel 210 of the syringe is in a fixed position with respect to the inner sleeve 206. A flange 210a of the barrel 210 can be positioned within a slot 240 of the inner sleeve 206 to retain the barrel 210 in position. The flange 210a can be integrally formed with the barrel 210 or, alternatively, can be a separate component that is secured to the barrel 210 by bonding or other procedure. In certain embodiments, the inner sleeve 206 includes more than one slot, each slot corresponding to a different dose volume. For example, one slot can correspond to a dose volume of 0.3 mg and a second slot can correspond to a dose volume of 0.15 mg. In such an embodiment, the slots are at different distances from the proximal end of the outer sleeve 204, which leads to the delivery of differing dose volumes. With the flange 210a disposed in the slot 240, the needle 212 extends at least partially from the distal end of the inner sleeve 206. This allows the cap 203 to engage the needle cover 213.

Figure 11:
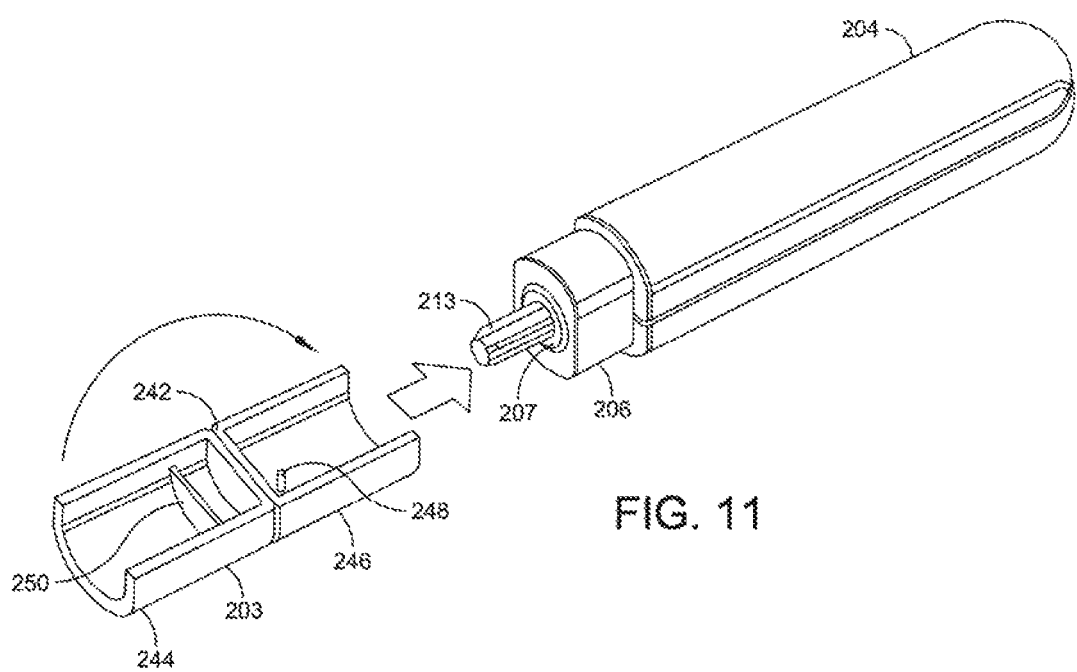
FIG. 11 is an isometric view of the injector of FIG. 9 prior to assembly of the cap onto the injector.
Figure 12:
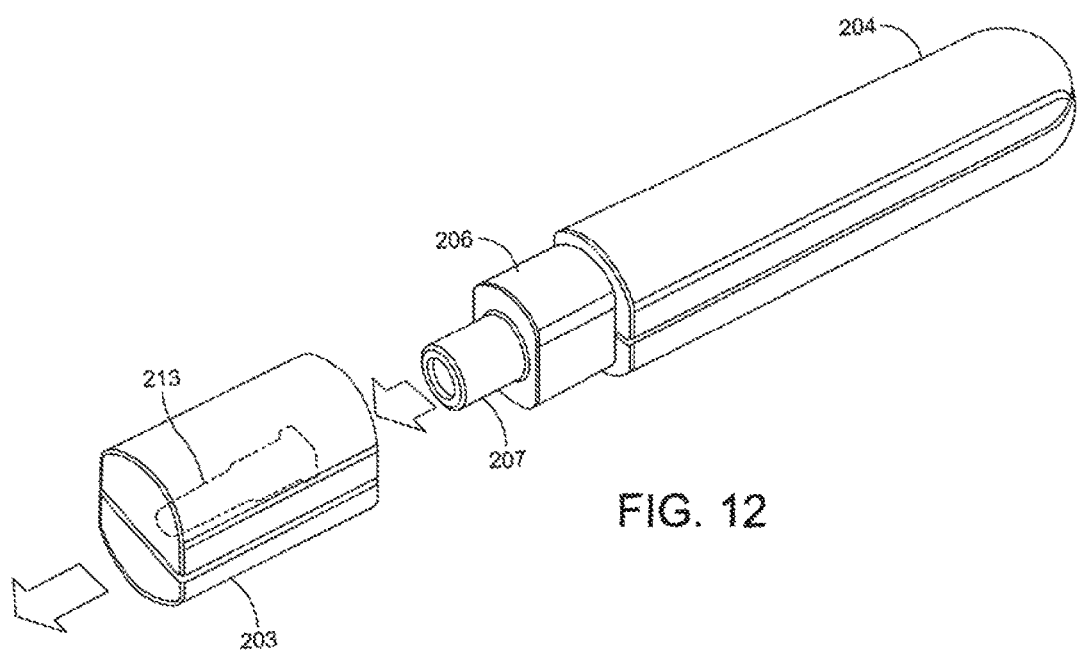
FIG. 12 is an isometric view of the injector of FIG. 9 after removal of the cap and needle cover from the injector.

As shown in FIG. 11, the cap 203 includes features for engaging the needle cover 213 of the syringe 208. In one embodiment, the cap 203 is a clamshell design with a living hinge 242 connecting an upper portion 244 and a lower portion 246. The lower portion 246 includes a projection 248 and the upper portion 244 includes an inner wall 250. During assembly, the cap 203 is closed around the needle cover 213 and connected to the body 202. As the cap 203 is closed, the projection 248 and the inner wall 250 engage the needle cover 213. As a result, upon removal of the cap 203 from the body 202, the needle cover 213 is removed from the syringe 208, as shown in FIG. 12.

As the cap 203 is removed from the injector 200, the needle sleeve 207 translates in the distal direction relative to the inner sleeve 206. This may be caused by contact between the needle cover 213 and the needle sleeve 207. For example, a flange 213a (shown in FIG. 10) of the needle cover 213 may contact the needle sleeve 207 and pull the needle sleeve 207 out as the needle cover 213 is removed. As a result, the needle sleeve 207 covers the needle 212 and prevents inadvertent needle stick injuries. The needle sleeve 207 can provide a visual indicator, such as a contrasting color, to alert the user that the injector has not yet been used and that a needle is contained therein.

During insertion, the needle sleeve 207 is able to translate in the proximal direction with respect to the inner sleeve 206 to expose the needle 212 for insertion into the target. Continued force applied to the outer sleeve 204 causes injection of the medicament as described above.

Figure 13:
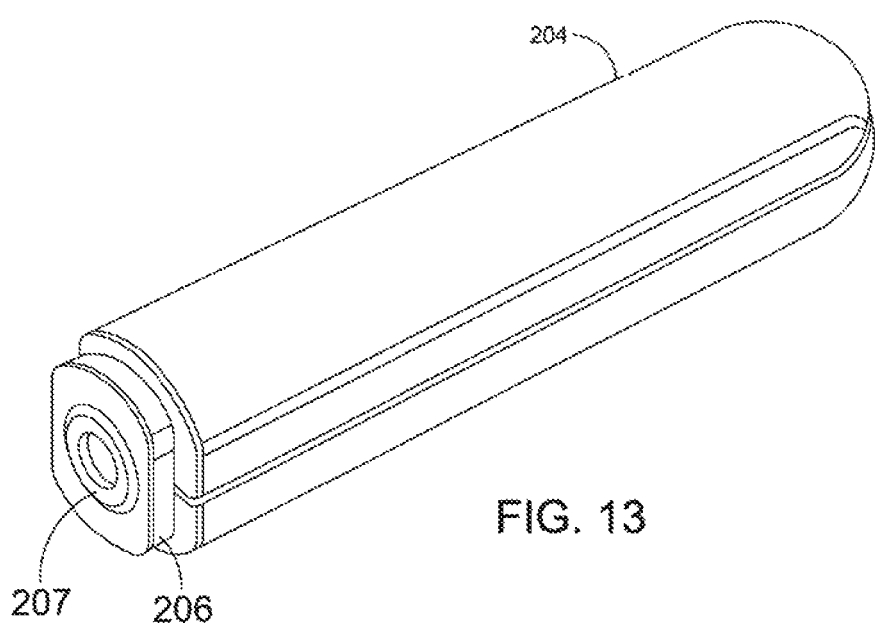
FIG. 13 is an isometric view of the injector of FIG. 9 after use.

Upon completion of the injection, the needle 212 of the syringe 208 retracts into the barrel 210 of the syringe 208. This embodiment does not require a biasing member to cause translation of the inner sleeve 206 in the distal direction with respect to the outer sleeve 204 after injection. Because the needle 212 is safely enclosed in the barrel, needle stick injuries are prevented and the needle 212 is not viewable by the user. The injector 200 is compact after use and occupies less space when discarded, as shown in FIG. 13. Optionally, the syringe 208 can be removed from the injector 200 and discarded in a sharps container. In certain embodiments, the injector 200 can then be reused for later injections with another syringe.

In another embodiment, as shown in FIGS. 14A-14E, an spray nozzle 300 is provided. The spray nozzle 300 can be attached to the injector 100 or the injector 200. The spray nozzle 300 includes a body 302 and a tip 304 disposed at the distal end of the body 302. The spray nozzle 300 can also include one or more finger flanges 306, which may be located at the proximal end of the body 302. The tip 304 includes one or more holes 308 at its distal end through which the medicament can exit.

The spray nozzle 300 allows for the medicament to be delivered intranasally, which avoids the need for an insertion of a needle into the patient, which may be preferable for some patients, specifically those with a fear of needles. By delivering the medicament across the mucosal membrane, and to the patient's blood stream, the injector with spray nozzle 300 delivers an effective dose of delivery. This can be particularly useful for medicaments used to treat opioid overdoses, such as Naloxone.

The spray nozzle 300 engages with the injector such that the needle is disposed in the distal end of the spray nozzle 300. Upon distribution of the medicament through the needle by translating the outer sleeve relative to the inner sleeve, the medicament is compressed into a spray that can be delivered to the patient. By providing the spray nozzle 300, the medicament can be delivered either via the spray nozzle to the mucosal membranes or, alternatively, via the needle intramuscularly, subcutaneously, or at any other appropriate depth. This provides the user or patient with the an option at time of delivery, allowing them to choose the method of delivery which is more comfortable or effective for them. In certain embodiments, the spray nozzle 300 and injector 100 or injector 200 are provided in a kit, for example in a common package.

Figure 14A:
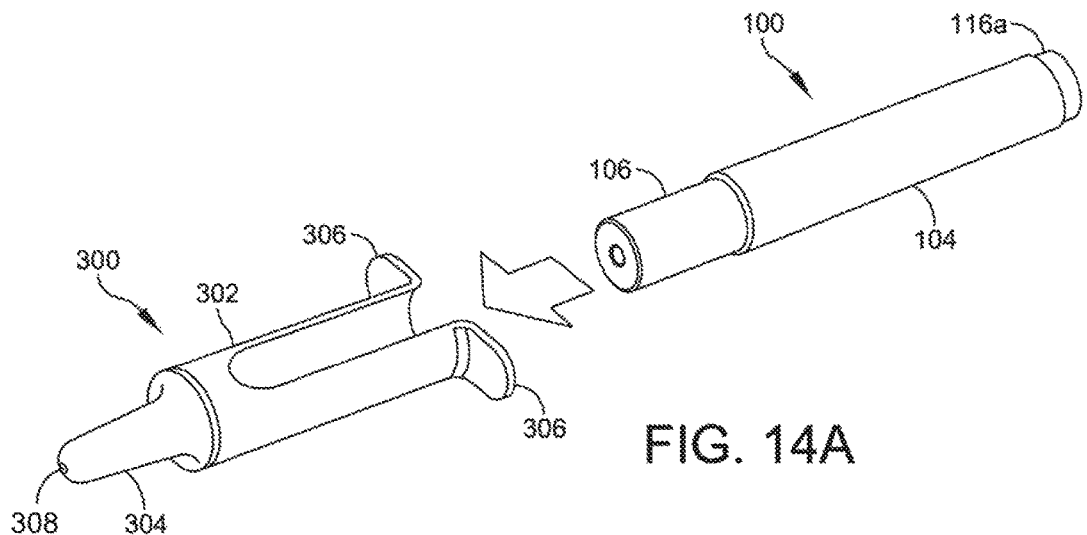
FIG. 14A is an isometric view of an injector and a spray nozzle.
Figure 14B:
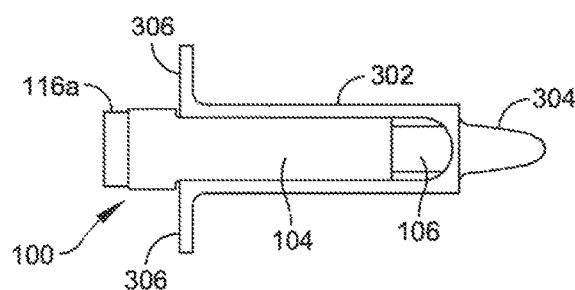
FIG. 14B is a side view of the injector and spray nozzle of FIG. 14A in an assembled configuration.
Figure 14C:
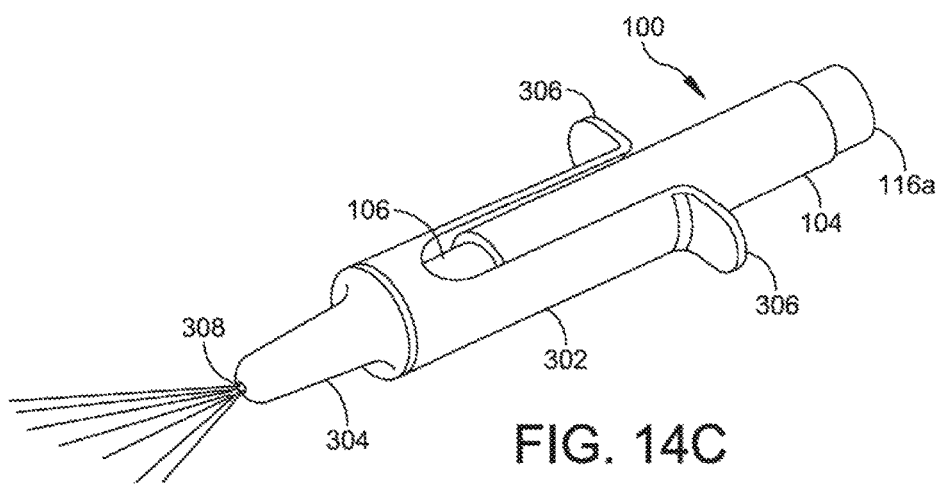
FIG. 14C is an isometric view of the injector and spray nozzle of FIG. 14A during use.
Figure 14D:
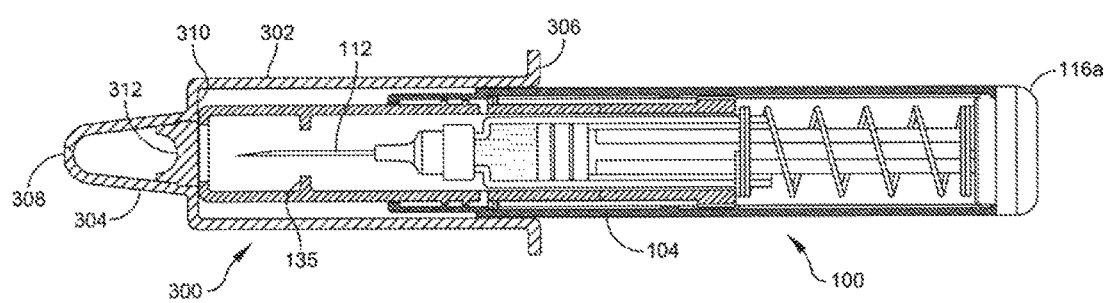
FIG. 14D is a cross-sectional view of the injector and spray nozzle of FIG. 14A in a first configuration.

In use, cap 103 is first removed from the body 102 of the injector 100 or 200. The spray nozzle 300 is placed on the body 102 such that the inner sleeve 106 or 206 abuts the distal end of the body 302 of the spray nozzle 300, as best shown in FIG. 14D. The distal end of the inner sleeve 106, 206 contacts a shoulder 310 within the spray nozzle 300. The tip 304 of the spray nozzle 300 is placed adjacent to, or at least partially within the nostril of the patient. A force is then applied to the outer sleeve 104 or 204 to cause it to axially translate with respect to the inner sleeve 106 or 206 and spray nozzle 300. This translation first causes the syringe 108 or 208 to translate to a position in which the needle 112 or 212 is at least partially within the tip 304 of the spray nozzle 300. Further translation of the outer sleeve 104 or 204 causes distribution of the medicament, as described above and as shown in FIG. 14C. When operating the injector, the user may hold the finger flanges 306 of the spray nozzle 300 to provide a counterforce.

Figure 14E:
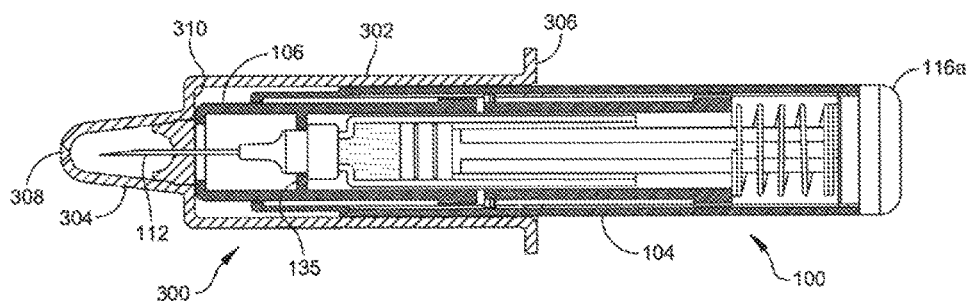
FIG. 14E is a cross-sectional view of the injector and spray nozzle of FIG. 14A in a second configuration.

In one embodiment, as shown in FIGS. 14D and 14E, a septum 312 is disposed within the tip 304 of the spray nozzle 300. In some embodiments, the septum 312 maintains the sterility of the inside of the tip 304 prior to use. Depression of the outer sleeve 104 with respect to the inner sleeve 106 causes the needle 112 to extend out of the inner sleeve 106 and pierce the septum 312. The septum 312 can be constructed of a material comprising an elastomer, a silicone, or any other appropriate material. Upon further translation of the outer sleeve 104, 204 toward the tip 304, the medicament is expelled. The septum 312 prevents the medicament from traveling in the proximal direction out of the tip 304. As a result, the contents of the syringe are expelled through the one or more holes 308.

Figure 15:
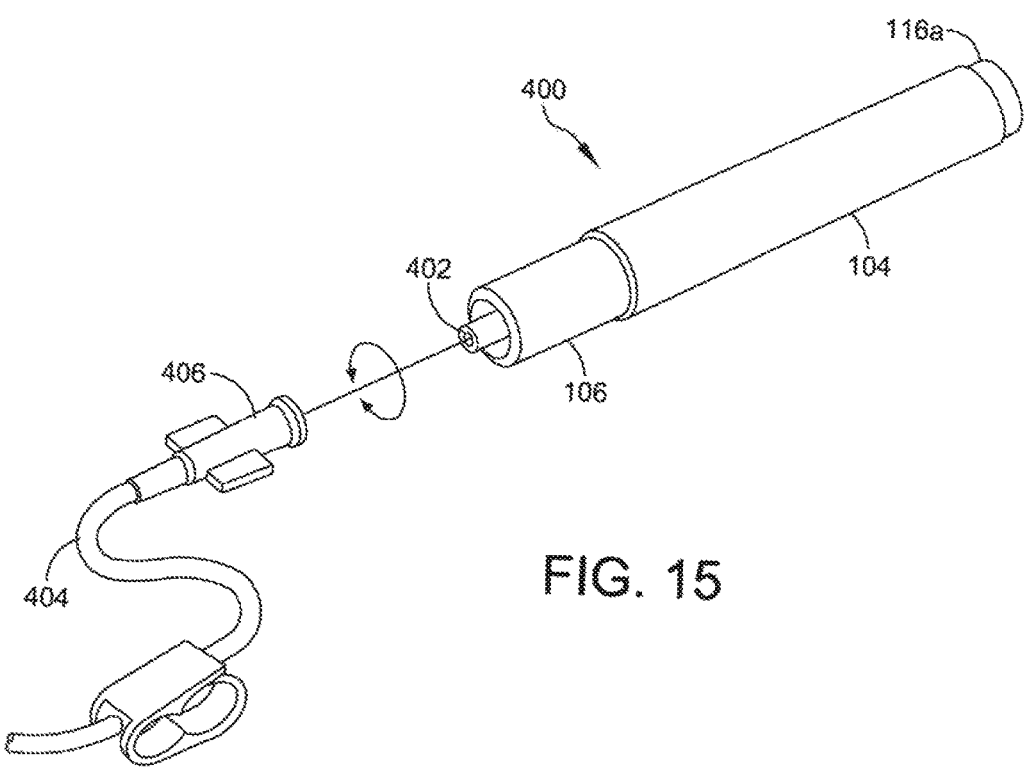
FIG. 15 is an isometric view of an injector having a luer connector and a tubing set

In another embodiment, as shown in FIG. 15, an injector 400 is provided in which the inner sleeve 106 has a luer connector 402 at its distal end. In other aspects, the injector can be substantially the same as the injector 100, described above. This allows the injector 400 to be connected to a tubing set 404 to allow the medicament to be delivered by, for example, an intravenous or intraosseous infusion device. The luer connector 402 can be a male luer connector for connection to a female luer fitment 406 of the tubing set. Alternatively, the luer connector 402 can be a female luer connector for connection to a male luer fitment. The injector 400 can be attached to the tubing set 404 using locking or slipping type Luer connections, such as those sold under the names LUER-LOK™ and LUER-SLIP™ by Becton Dickinson.

In operation, the cap 103 is removed from the body 102 of the injector 400. The luer fitment 406 is then attached to the luer connector 402. The medicament can then be delivered through the tubing set 404 by translating the outer sleeve 104 relative to the inner sleeve 106. This causes the medicament to be delivered through the luer connection, the tubing set 404, and to the patient.

Figure 16:
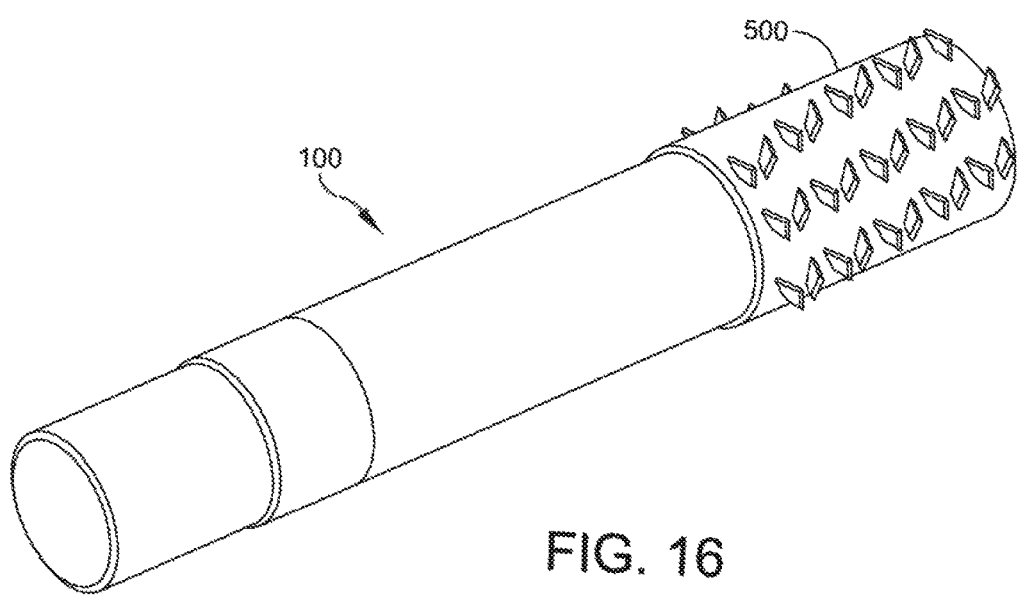
FIG. 16 is an isometric view of an injector having a grip.

As shown in FIG. 16, a grip 500 can be provided on the injector 100, 200, 400. The grip 500 can for example, be integrally formed on the outer sleeve 104, 204 or, alternatively, the grip 500 can be a separate component, such as a sleeve which is slid over the outer sleeve 104, 204. The grip 500 can be of any size. For example, the grip 500 can cover the entire outer sleeve 104, 204. Alternatively, the grip 500 can cover only a portion of the outer sleeve 104, 204. The grip 500 can be formed from any appropriate material. For example, the grip 500 can be molded from santoprene or other elastomeric material. The material can be chosen to increase the ability to handle the injector 100, 200, 400. The grip 500 can include a texture or pattern to further increase the ability to handle the injector 100, 200, 400. For example, the grip 500 can include raised diamonds or lines, similar to that used on diamond plate.

In embodiments in which the grip 500 is a separate component that is slipped over the outer sleeve 104, 204, the grip 500 can have a closed proximal end. This can further seal the proximal end of the injector 100, 200, 400 and prevent entrance of foreign particles or fluids.

A grip, such as that shown in FIG. 16, can be particularly advantageous when the injector is used by troops in combat situations. In these scenarios, the injector may need to be used in harsh and damp conditions by troops who are often wearing gloves. Hence, it may be difficult to grasp the injector securely. By providing an injector with a grip which is easy to grasp in even difficult conditions, the injector can be used more reliably in these potentially life-saving scenarios.

In another embodiment, a method of operating an injector is provided. The method includes the steps of placing a distal end of an inner sleeve against the target location. With the injector in place, a force is applied to an outer sleeve. Applying the force to the outer sleeve (i) causes axial translation of the outer sleeve and a syringe relative to the inner sleeve, (ii) causes a needle of a syringe to extend out from the distal end of the inner sleeve and into the target location, and (iii) causes the syringe to contact an engagement member of the inner sleeve. Subsequently, a continued force is applied to the outer sleeve. Applying the continued force to the outer sleeve causes translation of a plunger rod and a seal within the syringe to cause delivery of the medicament. After delivery of the medicament, the injector is removed from the target location. A biasing member applies a force on the inner sleeve to cause the inner sleeve to translate in the distal direction with respect to the outer sleeve to cover the needle of the syringe such that the inner sleeve is locked in place with respect to the outer sleeve.

In another embodiment, a method of operating an injector with a syringe having a retractable needle is provided. A cap of the injector is removed, wherein removal of the cap also removes a needle cover of the syringe. The method further includes the steps of placing a distal end of an inner sleeve against the target location. With the injector in place, a force is applied to an outer sleeve. Applying the force to the outer sleeve (i) causes axial translation of the outer sleeve and a syringe relative to the inner sleeve, (ii) causes a needle of a syringe to extend out from the distal end of the inner sleeve and into the target location, and (iii) causes the syringe to contact an engagement member of the inner sleeve. Subsequently, a continued force is applied to the outer sleeve. Applying the continued force to the outer sleeve causes translation of a plunger rod and a seal within the syringe to cause delivery of the medicament. After delivery of the medicament is complete, the needle is retracted into the barrel of the syringe.

In another embodiment, a method of using an injector and a spray nozzle to deliver a medicament intranasally is provided. A cap of the injector is first removed. The spray nozzle is engaged with the injector. A tip of the spray nozzle is placed within or adjacent to a nostril of the patient. An outer sleeve of the injector is translated toward the tip of the spray nozzle to expel the medicament through the tip of the spray nozzle and to the patient.

In another embodiment, a method of using an injector to deliver a medicament intravenously or intraosseously is provided. A cap of the injector is first removed. A luer connector of an inner sleeve is connected to a luer fitment. An outer sleeve of the injector is translated toward the luer fitment to deliver the medicament through the luer connector, through a tubing set, and to the patient.

While the foregoing description and drawings represent preferred or exemplary embodiments of the present invention, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof.

In addition, numerous variations in the methods/processes described herein may be made without departing from the spirit of the invention. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention. All patents and published patent applications identified herein are incorporated herein by reference in their entireties.

What is claimed is:

1. An injector for delivering a medicament comprising:
    an outer sleeve defining a longitudinal axis, the outer sleeve including a raised curb extending from an inner wall, wherein the raised curb extends along a path which has a longitudinal component and a circumferential component extending along the circumference of the outer sleeve;
    an inner sleeve disposed partially within the outer sleeve; and
    a syringe having a barrel, a needle mounted to the distal end of the barrel, a plunger rod, and a seal slidably mounted in the barrel, wherein the plunger rod is engaged with the outer sleeve in a fixed spatial relationship such that the plunger rod and the outer sleeve translate as a unit throughout operation of the injector;
    wherein the outer sleeve is disposed and configured for axial translation relative to the inner sleeve from a first configuration wherein the inner sleeve extends from the outer sleeve a first distance to a second configuration in which the inner sleeve extends from the outer sleeve a second distance that is less than the first distance, and further wherein in a third configuration the inner sleeve extends from the outer sleeve a third distance that is greater than the second distance and the inner sleeve is restricted from axially translating with respect to the outer sleeve.

2. The injector of claim 1, wherein the raised curb is at least partially disposed in a recess formed in the outer sleeve.

3. The injector of claim 1, wherein the inner sleeve includes a flex arm extending parallel to the longitudinal axis, the flex arm having a protrusion extending radially outward from the inner sleeve to engage the raised curb.

4. The injector of claim 3, wherein the protrusion travels along a first side of the raised curb as the outer sleeve translates from the first configuration to the second configuration, and wherein the protrusion travels along a second side of the raised curb as the outer sleeve translates from the second configuration to the third configuration.

5. The injector of claim 4, wherein travel along the first side of the raised curb causes deflection of the flex arm and wherein as the outer sleeve reaches the second configuration, the protrusion disengages the raised curb and contacts a strike face, thereby providing audible or tactile feedback to the user.

6. The injector of claim 3, wherein the flex arm is in an unstressed position when the outer sleeve is in the first configuration.

7. The injector of claim 3, wherein in the third configuration the protrusion is disposed between the raised curb and a locking member, thereby restricting relative translation of the inner sleeve and the outer sleeve.

8. The injector of claim 1, wherein the inner sleeve defines a distal end and a proximal end, and wherein the inner sleeve includes at least one engagement member extending from an inner wall of the inner sleeve at a position intermediate the distal end and the proximal end.

9. The injector of claim 1, further comprising a cap and the syringe further comprises a needle cover, wherein the cap is configured to engage the needle cover such that removal of the cap from the injector removes the needle cover from the syringe.

10. The injector of claim 1, further comprising a biasing member positioned proximally of the inner sleeve and configured to apply a force on the inner sleeve in a distal direction.

11. An injector for delivering a medicament comprising:
    an outer sleeve;
    an inner sleeve disposed partially within the outer sleeve, the inner sleeve defining a chamber between a distal end and a proximal end of the inner sleeve and having an engagement member extending into the chamber at a position between the distal end and the proximal end; and
    a syringe having a barrel, a needle mounted to the distal end of the barrel, a plunger rod, and a seal slidably mounted in the barrel, wherein the plunger rod is engaged with the outer sleeve in a fixed spatial relationship such that the plunger rod and the outer sleeve translate as a unit throughout operation of the injector;
    wherein the outer sleeve is disposed and configured for axial translation relative to the inner sleeve, and wherein in a first configuration the engagement member is spaced apart from the barrel of the syringe and wherein in a second configuration the syringe contacts the engagement member such that continued axial translation of the outer sleeve causes translation of the plunger rod relative to the barrel to cause delivery of the medicament through the needle.

12. The injector of claim 11, wherein only a portion of the needle extends from the inner sleeve when the engagement member is in contact with the barrel of the syringe.

13. The injector of claim 11, wherein the translation of the syringe from the first configuration to the second configuration is caused by a frictional force between the seal and the barrel.

14. The injector of claim 11, wherein the engagement member is integrally formed with the inner sleeve.

15. The injector of claim 11, wherein in the second configuration the needle extends from the inner sleeve a distance sufficient for subcutaneous delivery.

16. A method for operating an injector to deliver a medicament to a target location, the method comprising the steps:
    placing a distal end of an inner sleeve against the target location, wherein the inner sleeve is disposed at least partially within an outer sleeve;
    applying a force to the outer sleeve, wherein applying the force to the outer sleeve causes axial translation of the outer sleeve and a syringe relative to the inner sleeve, causes a needle of the syringe to extend out from the distal end of the inner sleeve and into the target location, and causes the syringe to contact an engagement member of the inner sleeve;

applying continued force to the outer sleeve causes translation of a plunger rod and a seal within the syringe to cause delivery of the medicament; and removing the injector from the target location, wherein a biasing member applies a force on the inner sleeve to cover the needle of the syringe such that the inner sleeve is locked in place with respect to the outer sleeve.

17. The method of claim 16, further comprising removing a cap from the injector and a needle cover from the syringe.

18. The method of claim 16, wherein after delivery of the medicament a flex arm of the inner sleeve contacts a strike face of the outer sleeve.

19. The method of claim 16, wherein the medicament is selected from the group consisting of epinephrine, naloxone, ketamine, diazepam, and biologics.

20. An injector for delivering a medicament comprising:
an outer sleeve defining a longitudinal axis;
an inner sleeve disposed partially within the outer sleeve, the inner sleeve defining a distal end and a proximal end, and wherein the inner sleeve includes at least one engagement member extending from an inner wall of the inner sleeve at a position intermediate the distal end and the proximal end; and
a syringe having a barrel, a needle mounted to the distal end of the barrel, a plunger rod, and a seal slidably mounted in the barrel, wherein the plunger rod is engaged with the outer sleeve in a fixed spatial relationship such that the plunger rod and the outer sleeve translate as a unit throughout operation of the injector;
wherein the outer sleeve is disposed and configured for axial translation relative to the inner sleeve from a first configuration wherein the inner sleeve extends from the outer sleeve a first distance to a second configuration in which the inner sleeve extends from the outer sleeve a second distance that is less than the first distance, and further wherein in a third configuration the inner sleeve extends from the outer sleeve a third distance that is greater than the second distance and the inner sleeve is restricted from axially translating with respect to the outer sleeve.

* * * * *

UNITED STATES PATENT AND TRADEMARK OFFICE
CERTIFICATE OF CORRECTION

PATENT NO. : 10,232,117 B2  
APPLICATION NO. : 15/755954  
DATED : March 19, 2019  
INVENTOR(S) : Thor Rollings Halseth Page 1 of 1

It is certified that error appears in the above-identified patent and that said Letters Patent is hereby corrected as shown below:

In the Claims

In Claim 16, at Column 15, Line 3: after "applying" and before "continued" please insert -- "a continued force to the outer sleeve, wherein applying the" --.

In Claim 16, at Column 15, Line 7: after "inner" and before "sleeve" please insert -- "sleeve to cause the inner sleeve to translate in the distal direction with respect to the outer" --.

Signed and Sealed this
Fourteenth Day of May, 2019

Andrei Iancu
*Director of the United States Patent and Trademark Office*